(12) United States Patent
Sampson

(10) Patent No.: US 12,004,975 B2
(45) Date of Patent: Jun. 11, 2024

(54) FLEXIBLE SOCKET INTERFACE

(71) Applicant: DBM, LLC, Rochester, MN (US)

(72) Inventor: Brandon Sampson, Pine Island, MN (US)

(*) Notice: Subject to any disclaimer, the term of this patent is extended or adjusted under 35 U.S.C. 154(b) by 0 days.

(21) Appl. No.: 16/968,558

(22) PCT Filed: Feb. 7, 2019

(86) PCT No.: PCT/US2019/017137
§ 371 (c)(1),
(2) Date: Aug. 7, 2020

(87) PCT Pub. No.: WO2019/157236
PCT Pub. Date: Aug. 15, 2019

(65) Prior Publication Data
US 2021/0038410 A1 Feb. 11, 2021

Related U.S. Application Data

(60) Provisional application No. 62/627,491, filed on Feb. 7, 2018.

(51) Int. Cl.
*A61F 2/80* (2006.01)
*A61F 2/76* (2006.01)
*A61F 2/78* (2006.01)

(52) U.S. Cl.
CPC .................. *A61F 2/80* (2013.01); *A61F 2/76* (2013.01); *A61F 2/7812* (2013.01); *A61F 2002/802* (2013.01)

(58) Field of Classification Search
CPC .. A61F 2/80; A61F 2/76; A61F 2/7812; A61F 2002/802
See application file for complete search history.

(56) References Cited

U.S. PATENT DOCUMENTS 8,114,167 B2 2/2012 Caspers
8,308,815 B2* 11/2012 McCarthy ............. A61F 2/7812
623/36

(Continued)

FOREIGN PATENT DOCUMENTS

WO 2017062690 A1 4/2017

OTHER PUBLICATIONS

Fatone, Stefania, and Ryan Caldwell. "Northwestern University Flexible Subischial Vacuum Socket for persons with transfemoral amputation—Part 1: description of technique." Prosthetics and orthotics international 41.3 (2017): 237-245. (Year: 2017).*

(Continued)

*Primary Examiner* — Jerrah Edwards
*Assistant Examiner* — Maximilian Tobias Spencer
(74) *Attorney, Agent, or Firm* — Fredrikson & Byron, P.A.

(57) ABSTRACT

An interface for use in conjunction with a prosthetic device is formed of a pliable material which is configured to support the necessary connection to a residual limb when used. The interface further has an internal surface structure that includes several stepped indentations which provide a more efficient and effective product. The stepped indentations have a dimension which decreases as the distance from the interior surface increases. In some embodiments, the indentations are shaped as an octagon, with each step also being octagonal. Other shapes are also contemplated. Also, the steps of the indentations could be uniform or irregular.

14 Claims, 4 Drawing Sheets

(56) References Cited

U.S. PATENT DOCUMENTS

| | | | |
|---|---|---|---|
| 8,668,744 B2* | 3/2014 | McCarthy | A61F 2/7812 |
| | | | 623/34 |
| 2007/0111625 A1* | 5/2007 | Morton | D21F 1/0063 |
| | | | 428/137 |
| 2009/0036999 A1 | 2/2009 | Egilsson et al. | |
| 2009/0240344 A1 | 9/2009 | Colvin et al. | |
| 2012/0191218 A1 | 7/2012 | McCarthy | |
| 2014/0363244 A1* | 12/2014 | Allen | B23B 51/009 |
| | | | 408/16 |
| 2015/0335079 A1* | 11/2015 | Lacey | A41D 13/015 |
| | | | 428/134 |
| 2016/0338858 A1 | 11/2016 | Hurley et al. | |
| 2018/0235779 A1* | 8/2018 | Dudding | A61F 2/7812 |
| 2019/0038439 A1 | 2/2019 | Caspers | |

OTHER PUBLICATIONS

"International Search Report and Written Opinion", Application No. PCT/US2019/017137, 13 pages.

* cited by examiner

FLEXIBLE SOCKET INTERFACE

BACKGROUND

As is well recognized, a human limb prosthetist typically includes a receptacle or socket which is custom designed to receive or accept an amputee's residual limb. In order to increase efficiency and provide comfort for the users, a liner and/or interface of some type is typically utilized. The liner or interface is typically formed from some type of an elastomeric material, thus providing certain levels of padding or cushion when used.

Several liners, interfaces and/or inserts exist and are currently in use. Many of these currently available devices have features designed to promote retention and comfort. That said, there is an additional need for an improved interface which can be used to enhance the connection to the residual limb when a vacuum feature is used. While other approaches have been developed, retention and comfort continue to be problematic. As an example, one existing approach has introduced small spikes or protrusions extending inwardly from a smooth inner surface which is specifically designed to interact with the residual limb. While this does provide some advantages, it is prone to creating irritation, blisters and pain due to the "irregular" surface interface provided, and inconsistencies with the donning process.

SUMMARY

An improved interface provides for added comfort and efficiency by adding an interior structure which provides the necessary interface. An interior surface structure provides this enhancement in a manner to avoid skin irritation and increase the retention capabilities of interface. In one particular embodiment, the indentations are formed as stepped structures, with the width of the indentations decreasing as the distance from the interior surface increases. In one embodiment, these indentations are shaped as an octagon. Other embodiments include many shapes and/or configurations, including but not limited to circular, rectangular, hexagon, oval, or any type of irregular shapes.

As mentioned above, the internal surface of the indentations in certain embodiments includes a stepped structure. This generally includes a uniform stepping, but could also include irregular or non-uniform steps. Aside from the particular details, it has been found that including stepped structures on the inner surface of these indentations provides more consistent holding force for the interface, while also avoiding issues of skin irritation.

BRIEF DESCRIPTION OF THE DRAWINGS

Further objects and advantages of the various embodiments can be seen by reviewing the following detailed description in conjunction with drawings in which.

DESCRIPTION OF THE PREFERRED EMBODIMENTS

Figure 1:
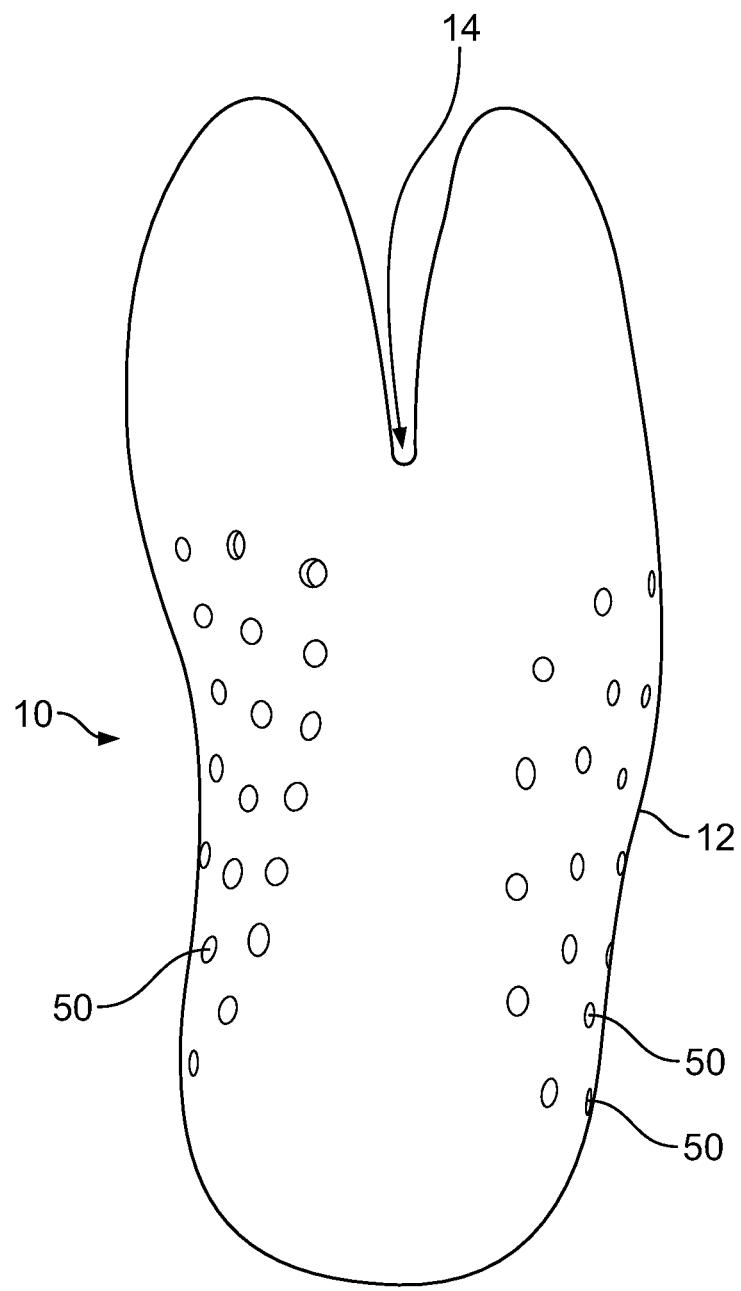
FIG. 1 is a front view of an embodiment of the flexible socket interface.
Figure 2:
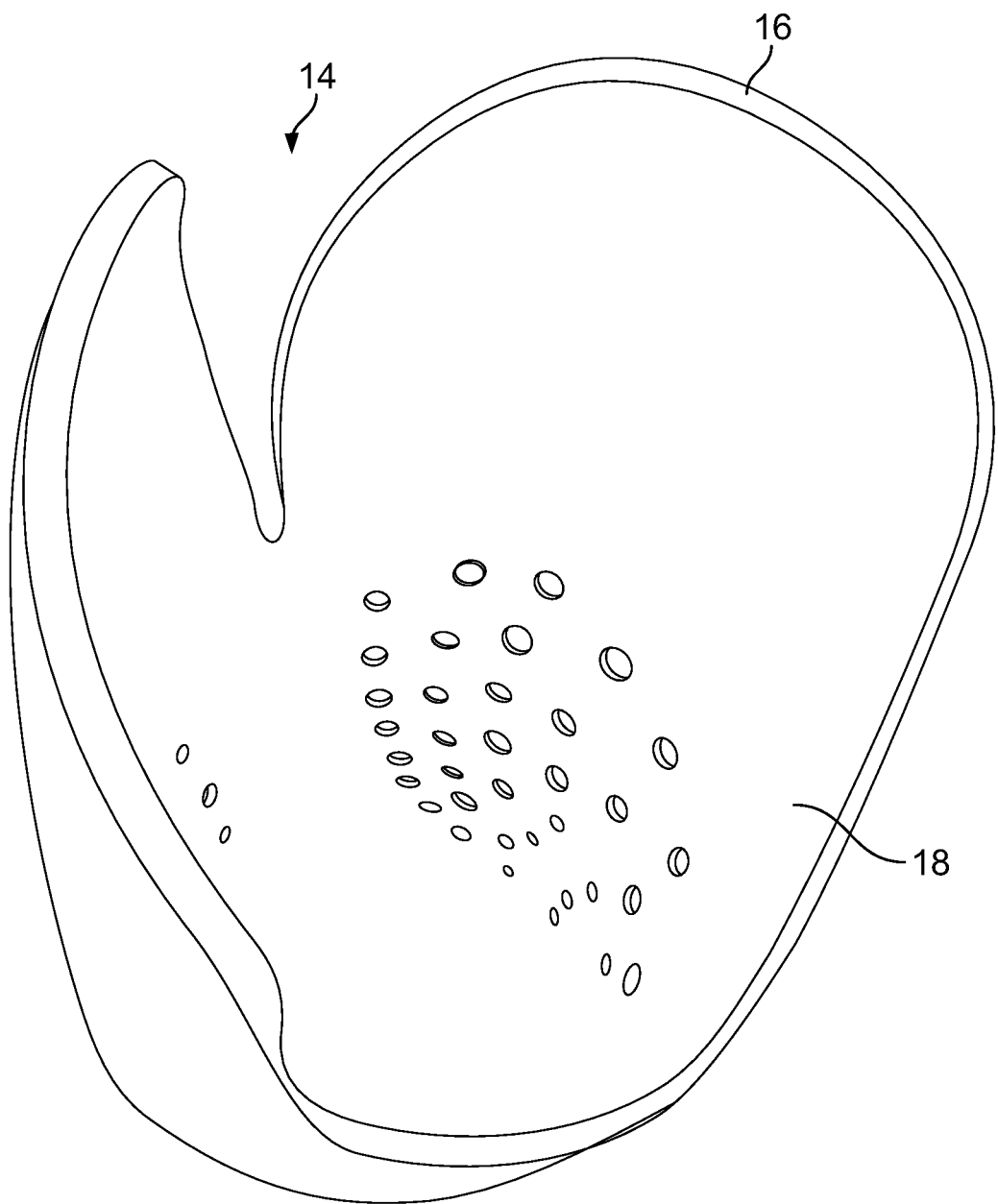
FIG. 2 is a top/inner view of the flexible socket interface.
Figure 3:
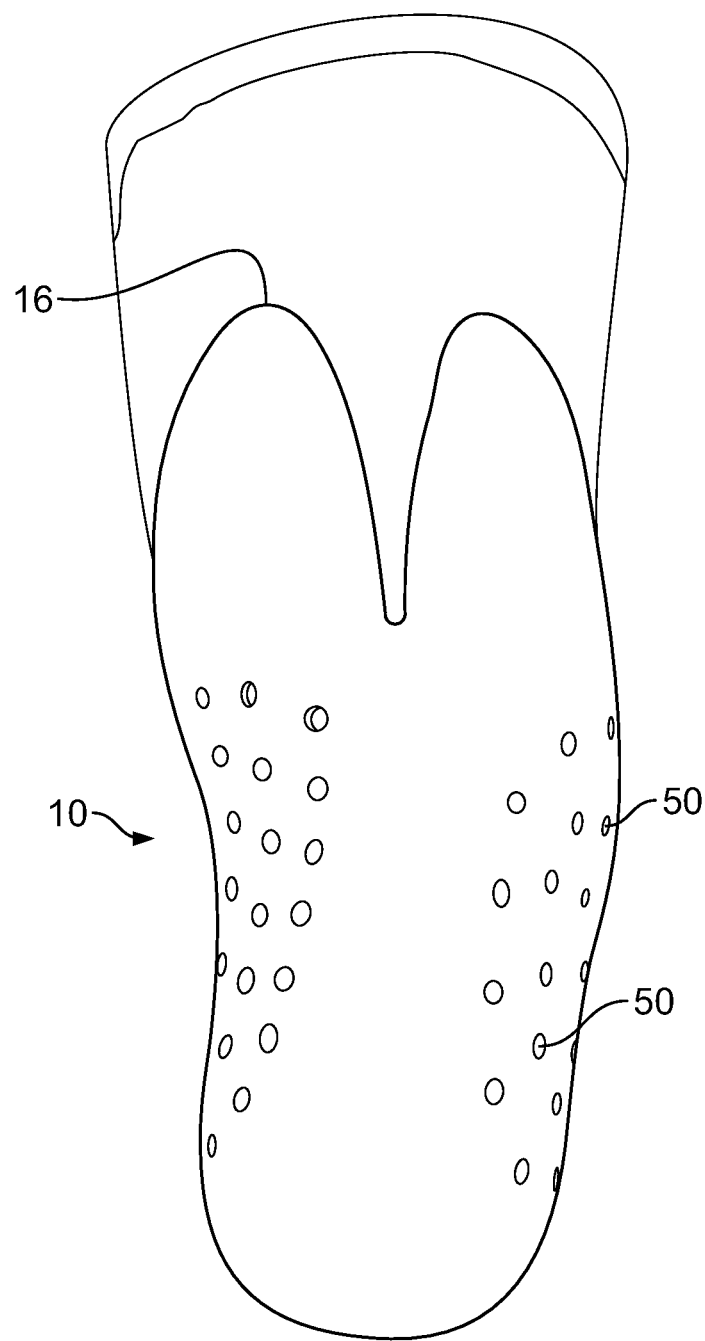
FIG. 3 is a second front view illustrating the flexible sock interface.

As illustrated in FIGS. 1-3, flexible socket interface 10 is a custom molded piece which will be specifically designed for each particular patient. Due to the custom nature of these devices, the actual configuration and overall shape of the flexible socket interface 10 will vary depending on the patient, needs, and particular issues involved. As appreciated, flexible socket interface 10 will have a wall structure 16, which includes an outer surface 12 and an inner surface 18. An open end 14 is specifically configured to receive the patient's residual limb. In FIG. 3, flexible socket interface 10 is shown fitted to a patient. As will be appreciated, interface 10 is designed and configured to be received with the socket (not shown) of a prosthetic limb.

As shown in FIGS. 1-3, flexible socket interface 10 includes a number of strategically placed and strategically shaped perforations 50. These perforations 50 are specifically configured to extend from the inner surface 18 to the outer surface 12. In use, an elevated vacuum is created to help retain the socket in place. In order to avoid discomfort, skin irritation and pain, socket interface 10 is configured to operate well in this elevated vacuum environment.

Figure 4:
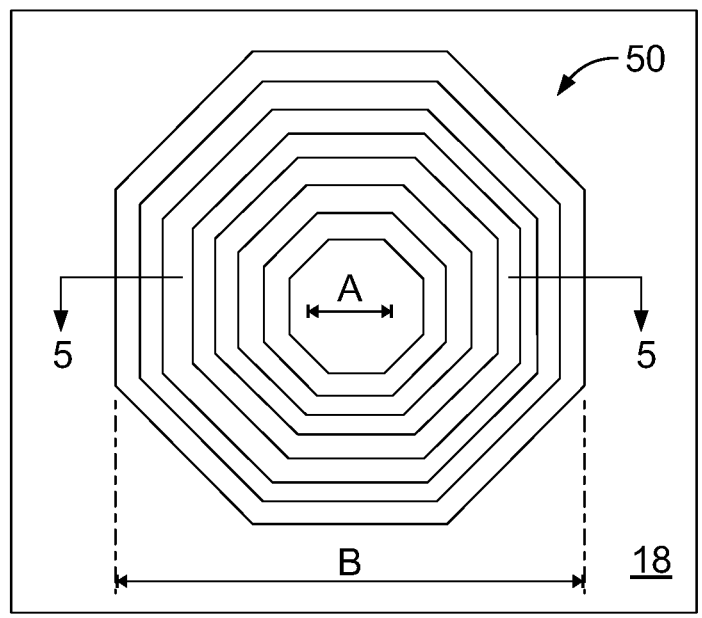
FIG. 4 is a bottom view of a interface perforation.
Figure 5:
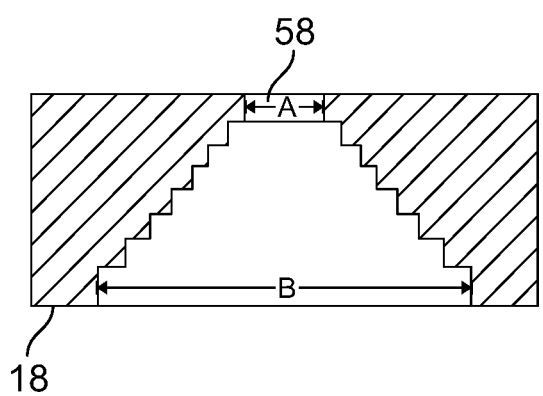
FIG. 5 is a cross sectional diagram of a portion of the flexible socket interface wall.

Referring now to FIGS. 4 and 5, an inside view (FIG. 4) and a cross sectional view (FIG. 5) of the interface wall 16 is shown. In these figures, one embodiment of the particular perforation 50 is better illustrated (which is not specifically shown in FIGS. 1-3). One embodiment is illustrated and discussed in detail, it is possible that many variations could exist.

Referring more specifically to FIG. 4 it will be seen that perforation 50 is shaped in a stepped octagon-type configuration. In this particular embodiment, a multi-step octagonal cut-out is provided for each perforation 50, with the dimensions growing smaller when moving away from inner surface 18. In this manner, the overall surface area of the perforation 50 (from an interior side) is increased, which provides several advantages. In this embodiment, each step is approximately one quarter of an inch. As also shown, the final portion extends completely through a surface area and creates an opening 58. As illustrated in this embodiment, each of the steps have square corners, although the corners could be slightly rounded.

It will be understood that some of the openings might not extend all the way through interface 10. In this situation, these openings would help with retention on the residual limb, but would not specifically interact with the socket. In certain instances, it may be beneficial to have indentations starting on the outer surface, thus further assisting in vacuum connections from other directions.

Again, flexible interface 10 is typically used in an elevated vacuum condition. Further, flexible interface 10 may be used in conjunction with a liner (not shown), which is placed over the residual limb. In this situation, the strategic placement and strategic configuration of openings will draw liner material into the internal cavities of perforations 50. This creates an improved interface. By drawing or pulling liner material into these cavities, increasing surface area connection, while substantially eliminating air gaps, thus creating better coupling and cooperation between the surfaces. Further, this eliminates drag, sheer and avoids the possibility for irritation and blisters when used.

Various materials could be utilized for the flexible socket interface, however it is contemplated that a material such as thermolyn or flexible material of some sort, would be used. Other possible materials clearly exist, such as certain silicon materials or other copolymers. The materials should be have a desired level of flexibility to promote the vacuum and sealing functions mentioned above.

Various embodiments of the invention have been described above for purposes of illustrating the details thereof and to enable one of ordinary skill in the art to make and use the invention. The details and features of the disclosed embodiment[s] are not intended to be limiting, as many variations and modifications will be readily apparent to those of skill in the art. Accordingly, the scope of the present disclosure is intended to be interpreted broadly and to include all variations and modifications coming within the scope and spirit of the appended claims and their legal equivalents.

The invention claimed is:

1. An interface for use in a prosthetic limb, comprising:
   a layer of interface material custom formed to fit a residual limb of a patient, the interface material having a plurality of perforations therein designed to accommodate a vacuum seal between the residual limb and a socket of a prosthetic limb, the perforations extending inwardly from an outer surface of the interface material to an inner surface;
   wherein each perforation has a stepped profile with a plurality of steps, with the cross sectional width of each perforation getting smaller moving away from the inner surface of the interface material toward the outer surface.

2. The interface of claim 1 wherein the planar configuration of each perforation is octagonal and each of the plurality of steps are also octagonal.

3. The interface of claim 1 wherein the layer of interface material is formed of a polymeric material.

4. The interface of claim 1 wherein the planar configuration of each perforation is circular and each stepped down portion is also circular.

5. The interface of claim 1 wherein a final step of the plurality of steps provides an opening to the outer surface of the liner.

6. The interface of claim 5 wherein the stepped configuration has at least three steps.

7. The interface of claim 1 wherein the interface material is pliable thus allowing partial deformation of the perforations when subject to a vacuum condition.

8. The interface of claim 1 wherein the interface is designed to be used in conjunction with a liner, and wherein the liner material will be drawn into the perforations when used within the socket and when subject to a natural vacuum condition created based upon a custom configuration of the liner, socket and interface.

9. The interface of claim 1 wherein each of the plurality of steps has a size of approximately one quarter of an inch.

10. An interface for use with a custom designed prosthetic limb to provide attachment to a residual limb of a user, the interface comprising:
    a custom fit layer of interface material configured to surround and capture the residual limb, the interface material having a plurality of perforations therein designed to accommodate a vacuum seal between the residual limb and a socket of the prosthetic limb, the perforations extending inwardly from an outer surface of the interface material to an inner surface;
    wherein each perforation is octagonal in shape with a stepped profile having a plurality of steps, with the cross sectional width of each perforation getting smaller moving away from the inner surface of the interface material toward the outer surface, thus causing an opening in the outer surface being smaller than the opening in the inner surface, the perforations helping to accommodate the vacuum seal by increasing surface area.

11. The interface of claim 10, wherein the interface material is a polymeric material.

12. The interface of claim 10 wherein the stepped configuration has at least three steps.

13. The interface of claim 10 wherein the interface material is pliable thus allowing partial deformation of the perforations when subject to a vacuum condition.

14. The interface of claim 10 wherein the interface is designed to be used in conjunction with a liner, and wherein the liner material will be drawn into the perforations when used within the socket and when subject to a natural vacuum condition created based upon a custom configuration of the liner, socket and interface.

* * * * *